United States Patent [19]

Burzin

[11] 4,317,942
[45] Mar. 2, 1982

[54] ODORIFEROUS 2-ALKOXYETHYL-CYCLOALKYL-ETHERS

[75] Inventor: Klaus Burzin, Marl, Fed. Rep. of Germany

[73] Assignee: Chemische Werke Huels, Aktiengesellschaft, Marl, Fed. Rep. of Germany

[21] Appl. No.: 167,601

[22] Filed: Jul. 11, 1980

[30] Foreign Application Priority Data

Jul. 13, 1979 [DE] Fed. Rep. of Germany ....... 2928348

[51] Int. Cl.³ .................. C07C 43/184; C07C 43/188
[52] U.S. Cl. ..................................... 568/670; 424/76; 252/522 R
[58] Field of Search .................. 568/670, 579; 424/76; 252/522 R

[56] References Cited

U.S. PATENT DOCUMENTS 3,281,474 10/1966 Leidig ................................. 568/579
3,845,141 10/1974 Naegeli .............................. 568/579
4,130,509 12/1978 Conrad et al. .................. 568/579 X

*Primary Examiner*—Bernard Helfin
*Attorney, Agent, or Firm*—Millen & White

[57] ABSTRACT

Odorferous 2-alkoxyethyl-cycloalkyl-ethers of the formula

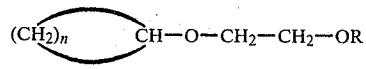

wherein
R is a saturated or unsaturated aliphatic hydrocarbon residue of 1-3 carbon atoms and
n is an integer of 5 to 11 are valuable odoriferous substances possessing a woodsy scent and good fixative properties.

5 Claims, No Drawings

ODORIFEROUS 2-ALKOXYETHYL-CYCLOALKYL-ETHERS

BACKGROUND OF THE INVENTION

The present invention relates to 2-alkoxyethyl-cycloalkyl-ethers which have valuable odoriferous properties.

SUMMARY OF THE INVENTION

It is an object of this invention to provide new compounds having odoriferous properties. Upon further study of the specification and appended claims, further objects and advantages of this invention will become apparent to those skilled in the art.

These objects have been attained by providing aliphatic ethers of the formula

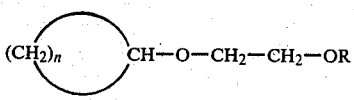

wherein
  R is a straight-chain or branched, saturated or unsaturated aliphatic hydrocarbon residue of 1–3 carbon atoms and
  n is an integer of 5 to 11. These are novel odoriferous substances (e.g., scenting agents, perfumes) having a woodsy scent and good fixative properties.

DETAILED DISCUSSION

The ethers of this invention are ordinarily prepared by etherification of the corresponding 2-hydroxyethyl-cycloalkyl-ethers. In this process, the conventional etherification methods can be utilized. See, for example Houben-Weyl, "Methoden der organischen Chemie" (Methods of Organic Chemistry) VI/3, Oxygen Compounds I, Part 3 pp. 10–137 (1965), whose disclosure is incorporated by reference herein.

The crude ethers so obtained are normally purified by fractional distillation. Removal of the final traces of nonetherified alcohols can also be accomplished by other separating processes, e.g. extraction or absorption processes.

The starting material 2-hydroxyethyl-cycloalkyl-ethers can be prepared, in principle, by ethoxylation of the corresponding conventional cycloalkanols with ethylene oxide or with ethylene carbonate under reaction conditions conventional for such ethoxylations. To increase the acidity of the secondary hydroxy group, it is recommended, in accordance with the process of German Patent No. 974,767, to add boron trifluoride. One drawback of this process is that the degree of ethoxylation will be greater than 1, thereby simultaneously forming polyethylene oxide.

In contrast, the production of the 2-hydroxyethyl-cycloalkyl-ethers by hydrogenation of the dioxolanes prepared from the cycloalkanones and ethylene glycol is substantially more selective, as described in British Pat. No. 1,125,730.

Among the ethers of this invention, the compounds wherein n=5, 7 and 11, and R=CH$_3$ and C$_2$H$_5$ have the greatest importance, the compounds with R=CH$_3$ being preferred. Other possible R groups include propyl, isopropyl, allyl, propargyl, etc.

Typical ethers of this invention include, for example, 2-methoxyethyl-cyclohexyl-ether, 2-ethoxyethyl-cyclohexyl-ether, 2-methoxyethyl-cyclooctyl-ether, 2-ethoxyethyl-cyclooctyl-ether, 2-methoxyethyl-cyclododecyl-ether, 2-ethoxyethyl-cyclododecyl-ether, etc.

The ethers of this invention can be blended with other compounds and materials, primarily with other odoriferous substances, in a great variety of quantitative ratios, to be determined in accordance with the finally desired odor, e.g., via routine preliminary tests, to obtain novel substance combinations and/or novel scenting agent compositions. In this connection, the proportion of the claimed ethers is generally up to 60% by weight, preferably 1–50% by weight.

Such odoriferous substance compositions include perfumes per se. The compounds of this invention can be used also for the perfuming of cosmetic agents, such as, for example, creams, toilet soaps, and lotions. In addition, they can be utilized to improve the scent of industrial products, such as, for instance, detergents, cleaning agents, disinfectants, textile assistants, etc., which otherwise possess an offensive odor.

The following examples explain the subject matter of the present invention in greater detail, without, however, restricting the invention, since the remaining aliphatic ethers can be prepared in a corresponding way and likewise exhibit the typical woodsy scent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2-Methoxyethyl-cyclododecyl-Ether 25 g of sodium amide was introduced into 150 ml of xylene and heated to boiling under agitation. Within one hour, 114 g (0.5 mol) of 2-hydroxyethyl-cyclododecyl-ether, dissolved in 750 ml of xylene, was allowed to drip into the boiling suspension. To complete the alcoholate formation, the mixture was heated under reflux for another two hours. Thereafter 44 g (0.35 mol) of dimethyl sulfate was added dropwise and the reaction mixture heated under reflux for another four hours. Then, the reaction mixture was poured into a mixture of ice and 35 g of sodium hydroxide. The organic phase was washed with water, dried over Na$_2$SO$_4$, and then fractionated.

| | |
|---|---|
| Boiling point | 105° C. at 0.05 mbar |
| Yield | 84% crude ether, 66% pure product |
| Index of refraction $n_{20}^D$ | 1.4713 |
| IR | 1100 cm$^{-1}$ |
| NMR (CCl$_4$) | δ 3.40 (S) (—O—CH$_2$—CH$_2$—O), δ 3.25 (S) (—O—CH$_3$) |

EXAMPLE 2

2-Ethoxyethyl-cyclododecyl-Ether

The 2-ethoxyethyl-cyclododecyl-ether was prepared in correspondence with the description of Example 1 from 114 g (0.5 mol) of 2-hydroxyethyl-cyclododecyl-ether and 54 g (0.35 mol) of diethyl sulfate.

| | |
|---|---|
| Boiling point | 109° C. at 0.05 mbar |
| Yield | 89% crude ether, 72% pure product |
| Index of refraction | |
| $n_{20}^D$ | 1.4688 |
| NMR (CCl$_4$) | δ 3.38 (Q) (—O—CH$_2$—CH$_3$), |
| | δ 3.40 (S) (—O—CH$_2$—CH$_2$—O) |

EXAMPLE 3

2-Methoxyethyl-cyclooctyl-Ether

According to the disclosure in Example 1, the 2-methoxyethyl-cyclooctyl-ether was obtained by reacting 86 g (0.5 mol) of 2-Hydroxyethyl-cyclooctyl-ether with 44 g (0.35 mol) of dimethyl sulfate.

| | |
|---|---|
| Boiling point | 58° C. at 0.1 mbar |
| Yield | 86% crude ether, 69% pure product |
| Index of refraction $n_{20}^D$ | 1.4617 |
| IR | 1100 cm$^{-1}$ |
| NMR (CCl$_4$) | δ 3.42 (S) (—O—CH$_2$—CH$_2$—O), |
| | δ 3.25 (S) (—O—CH$_3$) |

EXAMPLE 4

2-Ethoxyethyl-cyclooctyl-Ether

The 2-ethoxyethyl-cyclooctyl-ether was produced in correspondence with the description in Example 1 by reacting 86 g (0.5 mol) of 2-hydroxyethyl-cyclooctyl-ether with 54 g (0.35 mol) of diethyl sulfate.

| | |
|---|---|
| Boiling point | 84° C. at 0.5 mbar |
| Yield | 94% crude ether, 75% pure product |
| Index of refraction | |
| $n_{20}^D$ | 1.4583 |
| IR | 1100 cm$^{-1}$ |
| NMR (CCl$_4$) | δ 3.42 (S) (—O—CH$_2$—CH$_2$—O), |
| | δ 3.39 (Q) (—O—CH$_2$—CH$_3$) |

EXAMPLE 5

2-Methoxyethyl-cyclohexyl-Ether

According to the procedure set forth in Example 1 the 2-methoxyethyl-cyclohexyl-ether was produced from 72 g (0.5 mol) of 2-hydroxyethyl-cyclohexyl-ether and 44 g (0.35 mol) of dimethyl sulfate.

| | |
|---|---|
| Boiling point | 46° C. at 0.4 mbar |
| Yield | 88% crude ether, 76% pure product |
| Index of refraction | |
| $n_{20}^D$ | 1.4428 |
| IR | 1100 cm$^{-1}$ |
| NMR (CCl$_4$) | δ 3.42 (S) (—O—CH$_2$—CH$_2$—O), |
| | δ 3.25 (S) (—O—CH$_3$) |

EXAMPLE 6

2-Ethoxyethyl-cyclohexyl-Ether

The 2-ethoxyethyl-cyclohexyl-ether was prepared in correspondence with the description of Example 1 from 72 g (0.5 mol) of 2-hydroxyethyl-cyclohexyl-ether and 54 g (0.35 mol) of diethyl sulfate.

| | |
|---|---|
| Boiling point | 46° at 0.1 mbar |
| Yield | 87% crude ether, 71% pure product |
| Index of refraction | |
| $n_{20}^D$ | 1.4422 |
| IR | 1100 cm$^{-1}$ |
| NMR (CCl$_4$) | 3.43 (S) (—O—CH$_2$—CH$_2$—O), |
| | 3.41 (Q) (—O—CH$_2$—CH$_3$) |

The following examples relate to odoriferous substance composition which contain compounds of this invention.

EXAMPLE 7 (Woodsy Note)

| | Parts by Weight |
|---|---|
| 2-Methoxyethyl-cyclododecyl-ether | 250 |
| Sandalwood oil | 350 |
| Bergamot oil | 100 |
| Vetiver oil | 50 |
| Amyl salicylate | 80 |
| Coumarin | 50 |
| Rose oil | 50 |
| Heliotropin | 50 |
| Xylene musk | 20 |
| | 1,000 |

EXAMPLE 8 (Woodsy Note)

| | Parts by Weight |
|---|---|
| 2-Ethoxyethyl-cyclododecyl-ether | 500 |
| Sandalwood oil | 100 |
| Vetiveryl acetate | 100 |
| Oryclon (Haarmann + Reimer) | 100 |
| Coumarin | 50 |
| Guaiyl acetate | 50 |
| 2-Phenylethanol | 50 |
| Isoraldein 70 (L. Givaudan) | 50 |
| | 1,000 |

EXAMPLE 9 (Phantasy Perfume)

| | Parts by Weight |
|---|---|
| 2-Ethoxyethyl-cyclooctyl-ether | 350 |
| Anisaldehyde | 150 |
| Lavender oil | 100 |
| Geranium oil | 100 |
| Cedar leaf oil | 100 |
| Butyl phenylacetate | 50 |
| Hydroxycitronellal | 50 |
| Methyl naphthyl ketone | 50 |
| Benzyl acetate | 35 |
| Xylene musk | 15 |
| | 1,000 |

In the odoriferous substance compositions disclosed by way of example, it is also possible to use, instead of the aforementioned 2-alkoxyethyl-cycloalkyl-ethers, the other compounds of this invention, although in such a case there will be shifts in the scent nuances.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 2-alkoxyethyl-cycloalkyl-ether of the formula

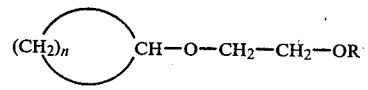

wherein
R is a saturated or unsaturated aliphatic hydrocarbon residue of 1-3 carbon atoms and
n is an integer of 5 to 11.

2. A 2-alkoxyethyl-cycloalkyl-ether of claim 1, wherein n is 5, 7 or 11.

3. A 2-alkoxyethyl-cycloalkyl-ether of claim 2, wherein n is 5 and R is $CH_3$, $C_2H_5$ or i-$C_3H_7$.

4. A 2-alkoxyethyl-cycloalkyl-ether of claim 2, wherein n is 7 and R is $CH_3$, $C_2H_5$, i-$C_3H_7$, $CH_2$—CH=$CH_2$ or CH=CH—$CH_3$.

5. A 2-alkoxyethyl-cycloalkyl-ether of claim 2, wherein n is 11 and R is $CH_3$ or $C_2H_5$.

* * * * *